Figure 1:
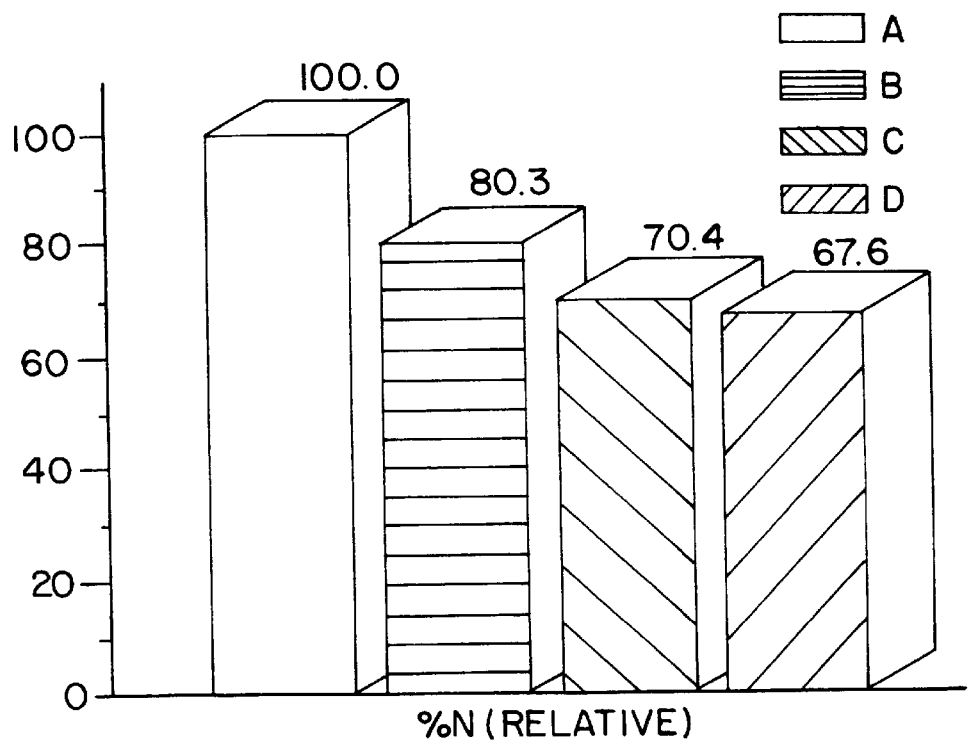
Figure 2:
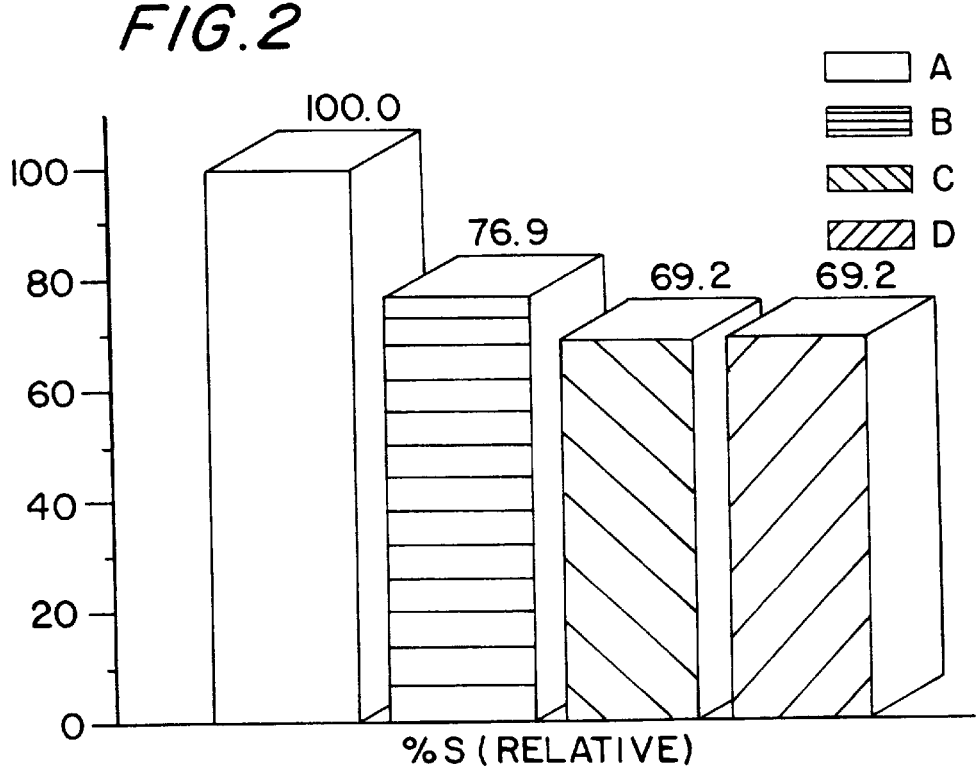

United States Patent [19]
Kripp et al.

[11] Patent Number: 6,153,196
[45] Date of Patent: Nov. 28, 2000

[54] USE OF FLOWER WAX IN LIQUID HAIR-TREATMENT AGENTS

[75] Inventors: Thomas Kripp, Fraenkisch-Crumbach; Beate Krause, Hattersheim; Guenther Lang, Reinheim; Wolfgang Maurer, Lampertheim; Ingrid Toeche-Mittler, Darmstadt, all of Germany

[73] Assignee: Wella Aktiengesellschaft, Darmstadt, Germany

[21] Appl. No.: 09/068,419

[22] PCT Filed: Oct. 4, 1997

[86] PCT No.: PCT/EP97/05459

§ 371 Date: May 13, 1998

§ 102(e) Date: May 13, 1998

[87] PCT Pub. No.: WO98/16188

PCT Pub. Date: Apr. 23, 1998

[30] Foreign Application Priority Data

Oct. 13, 1996 [DE] Germany .................. 196 41 992

[51] Int. Cl.$^7$ ...................................................... A61K 35/78
[52] U.S. Cl. ........................................................ 424/195.1
[58] Field of Search ........................................... 424/195.1

[56] References Cited

U.S. PATENT DOCUMENTS 5,460,808  10/1995  Mausner ................................. 424/70.7

FOREIGN PATENT DOCUMENTS 59 021 608   2/1984   Japan .
WO 93/17083  9/1993   WIPO .

*Primary Examiner*—Jean C. Witz
*Attorney, Agent, or Firm*—Michael J. Striker

[57] ABSTRACT

The use of flower wax, preferably from flowers of the jasmine, the mimosa, the narcissus, the bitter orange or the wild camomile in liquid hair treatment agents, as well as liquid hair treatment agents containing flower wax.

7 Claims, 1 Drawing Sheet

USE OF FLOWER WAX IN LIQUID HAIR-TREATMENT AGENTS

The invention relates to the use of flower wax in liquid hair treatment agents, as well as liquid hair treatment agents containing flower wax.

It is commonly known that natural plant waxes such as carnauba wax or candelilla wax have already found multiple uses in cosmetic preparations. From the published international patent application WO 93/17083 the use of apple wax for the production of cosmetic conditioning and cleansing agents for skin and hair is already known. The valuable properties of these already carefully researched natural plant waxes have in the meantime led to the development of modern extraction methods allowing for a good yield of isolated plant waxes free of interfering impurities.

While essential oils that can be isolated from natural flowers have received a particularly strong interest for the production of fragrances and perfumes, the waxes that can be isolated from natural flowers have found only little attention until now. More in-depth research has shown, however, that waxes isolated from natural flowers combine a plurality of valuable properties that could lead to expectations of increased future commercial significance for these type of waxes.

Similar to all natural plant waxes, flower waxes also distinguish themselves by having hydrophobic properties, such as melting and emulsifying properties and biodegradability. Particularly with flower wax these properties are now additionally combined with technically applied parameters which provide good prerequisites for use in hair treatment agents.

In the Japanese published patent application 21 608 of 1984 main treatment products (cream, lipstick) and a solid hair stick are described as containing jasmine flower wax. Liquid hair treatment agents have not been mentioned.

The subject of the invention is therefore a liquid hair treatment agent containing a wax isolated from natural flowers. Particularly the wax of such flowers as jasmine (*Jasminum officinale*), mimosa (*Mimosa pudica*), narcissus (Narcissus sp.), bitter orange (*Ponciurus trifoliata*) and wild camomile (*Matricaria chamomilla*) have already been closely researched and have demonstrated remarkable and valuable properties.

Noticeable in such preparations is the high absorption rate into the hair. Even minimal concentrations already have a marked conditioning effect on the hair. In addition, a significant luster and a marked neutralization of worked-in fragrances can be noticed in the cosmetic hair preparations. In addition, a liquid hair treatment agent containing flower wax is distinguished by its dermatological compatibility, its good moisturizing capacity and its oil-restoring effect, e.g. in hair cleansing lotions. These effects are achieved when the liquid hair treatment agent has a flower wax content in a quantity of 0.001 to 20 weight-percent, preferably in a quantity of 0.01 to 12 weight-percent, and particularly preferably in a quantity of 0.03 to 2 weight-percent. Flower waxes are therefore particularly applicable for the use of hair conditioners, shampoos, styling preparations, hair treatment agents made of foam, hair coloring agents, hair sprays and hair lotions. In this case the flower waxes are used in combination with all conventional cosmetic raw ingredients for liquid hair treatment agents, with the exception, however, of strongly oxidizing substances such as hydrogen peroxide. The liquid hair treatment agents can particularly be in the form of a solution, a water-in-oil or oil-in-water (w/o or o/w) emulsion, or a liquid gel or foam.

Proof of the characteristic absorption rate of the flower wax leading to the protective and conditioning effect of the hair can clearly be demonstrated by means of x-ray photoelectron spectroscopy (XPS). This is a surface sensitive measuring technology which makes it possible to determine the composition of elements and the compound condition of the elements in the outer-most molecular layer (information depth a few nanometers). For surface analytical investigations in the area of corrosion, metallurgy, catalysis, adhesion, microelectronics, and polymer technology, x-ray photoelectron spectroscopy has been useful for a relatively long period of time. However, it also has proven itself in research into complex fiber structures, for example wool, so that XPS measurement of such materials is now standard. This method is also suitable, however, for the surface evaluation of hair surfaces that have been treated with conditioning preparations, since their elementary composition can be determined to a depth of approximately 10 nm. The result of a hair surface measurement conducted by the XPS method is the elementary composition in atom % carbon (C), atom % oxygen (0), atom % nitrogen (N) and atom % sulphur (S) of the hair surface in a layer thickness of approximately 10 nm. Particularly the measuring results concerning surface content in atom % of nitrogen and sulphur are characteristic for the hair keratin, which is a protein.

If the hair surface is covered with a conditioning preparation showing in its composition essentially the elements of carbon and oxygen, however, only small parts or none at all of nitrogen or sulphur, then the parts (in atom %) of sulphur and nitrogen on the measured surface, depending on the grade of absorption capacity of the conditioning preparation, have to decline, since only the outer 10 nm layer thickness of the hair can be captured by XPS. The content (in atom %) of sulphur and nitrogen of the treated hair surface with a conditioning preparation is thus a measurement for the absorption capacity of the hair conditioning preparation. The lower the sulphur and nitrogen content (in atom %) as part of the elementary composition of the treated hair surface, the more even and denser is the film left on the surface by the conditioning preparation and the higher is also the absorption capacity of the hair conditioning preparation.

The use of x-ray photoelectron spectroscopy for the examination of the absorption capacity of the hair conditioning preparation was conducted in such a way, that the commercially used basic conditioning formula was changed by exchanging the fatty alcohol contained therein with 1% of apple, jasmine or mimosa wax respectively with the absorption capacity on the hair of the changed formula then being measured. In this case, the basic conditioning formula and the changed formula with the added flower wax each was left to react on the hair for 5 minutes, then the hair was thoroughly rinsed. As measurement of the formation of the protective film the reduced protein-typical elements "nitrogen" and "sulphur" detected by way of the conditioning formula were evaluated. The comparative formula with apple wax which had already been developed earlier, in this case was a test formula categorized as having a particular high valency for comparison, having reached a protective effect that previously had not by far come close to other tested cosmetic lipids. Surprisingly it showed however, that the absorption capacity of jasmine wax exceeds the absorption capacity of apple wax by more than 10%. The XPS measurements showed that the hair treated with the apple wax product in comparison to hair treated with jasmine wax had 19% more nitrogen and 11% more sulphur on its surface.

FIG. 1 shows a quantitative table of the elementary composition of the hair surface in atom % for nitrogen and sulphur, wherein the individual atom concentration for both elements has been set at 100% using the basic formula A. If the basic formula (A) only contains 1% apple wax (B), mimosa wax (C) or jasmine wax (D) the quantity of the surface-exposed hair protein when compared with the basic formula (A) decreases by more than 30%. The basic formula (A) here has the following composition:

TABLE 1

Composition of the Basic Formula

| Raw Ingredients | Formula A in % | Formula B in % | Formula C in % | Formula D in % |
|---|---|---|---|---|
| Cetyl Alcohol | 2.0 | 2.0 | 2.0 | 2.0 |
| Paraffin Oil | 2.0 | 1.0 | 1.0 | 1.0 |
| Apple Wax | — | 1.0 | — | — |
| Mimosa Wax | — | — | 1.0 | — |
| Jasmine Wax | — | — | — | 1.0 |
| Sorbitol Stearate | 1.0 | 1.0 | 1.0 | 1.0 |
| Lanolin Oil, Iso-propyl palmitate Castor Oil | 1.0 | 1.0 | 1.0 | 1.0 |
| Glycerin | 2.0 | 2.0 | 2.0 | 2.0 |
| Lauryl alcohol polyethylene glycolic ether (20 EO) | 1.0 | 1.0 | 1.0 | 1.0 |
| Cetyltrimethyl-ammonium chloride solution 25% | 2.0 | 2.0 | 2.0 | 2.0 |
| Water | 89.0 | 89.0 | 89.0 | 89.0 |

Further, it was noted that by exchanging carnauba or candelilla wax in the basic formula with each of the aforementioned flower waxes, an improvement in combability was obtained. A particularly marked effect could be registered in the case of bitter orange flower wax. Although in the case of narcissus wax a minor improvement of combability was achieved when comparing it with all the effects of the examined flower waxes, however, the hair in turn showed increased volume and a marked increase in stability of the hair style. Camomile wax resulted in an increase of luster.

The flower waxes used in accordance with the invention are obtained in unpurified form as raw materials waste from the production of perfume oil/aromatics. The raw waxes are however in need of additional purification in order to eliminate remaining chlorophylls, fragrances and polar impurities. This additional purification takes place in accordance with commonly known physical absorption methods as for example described in the international patent application WO 93/17083 for the purification of apple wax. For suitable purposes the raw wax first is dissolved in hot hexane, then stirred with fuller's earth under reflux temperature and finally left standing without stirring and heating until the fuller's earth loaded with impurities has settled. Subsequently the still warm deposit is filtered and the filtrate is freed of solubilizers by way of distillation. The physical dates of the used flower waxes in accordance with the invention can be derived from Table 3.

TABLE 3

Numerical Characteristics of the Flower Waxes

| Flower Waxes | Jasmine | Mimosa | Bitter Orange | Wild Camomile | Narcissus |
|---|---|---|---|---|---|
| Dripping Point [° C.] | 62.4 | 69.3 | 59.9 | 67.0 | 63.4 |
| Iodine number [g I/100 g] | 37.9 | 26.1 | 70 | 71 | 66 |
| Peroxide number | <1.0 | 3.9 | 32 | 41 | 29 |
| Acid number [mg KOH/g] | 2.0 | 13.0 | 9 | 20 | 7 |
| Saponification Number (KOH/g) | 68.0 | 59.0 | 96 | 99 | 51 |
| Ester number (SV − AV) | 66.0 | 46.0 | 87 | 79 | 44 |

The following examples show the possibilities of use of flower waxes in liquid hair treatment agents.

Example 1—Hair Spray Application in a Humid Climate

| Raw Ingredients | % | % | % | % | % | % |
|---|---|---|---|---|---|---|
| Vinyl acetate/croton acid-copolymer | 2.00 | 2.00 | 2.00 | 2.00 | 2.00 | 2.00 |
| 2-Amino-2-methyl-1-propanol | 0.16 | 0.16 | 0.16 | 0.16 | 0.16 | 0.16 |
| Ethyl Alcohol-non-aqueous | 37.84 | 37.84 | 37.84 | 37.84 | 37.84 | 37.84 |
| Perfume Oil | 0.10 | 0.10 | 0.10 | 0.10 | 0.10 | 0.10 |
| Carnauba Wax | 0.05 | | | | | |
| Jasmine Wax | | 0.05 | | | | |
| Mimosa Wax | | | 0.05 | | | |
| Bitter Orange Flower Wax | | | | 0.05 | | |
| Narcissus Wax | | | | | 0.05 | |
| Wild Camomile Wax | | | | | | 0.05 |
| Propyl Alcohol/Butane to make | 100.0 | 100.0 | 100.0 | 100.0 | 100.0 | 100.0 |

The substitution of flower wax for the carnauba wax leads to an improved combability and an increased stability of the hair style.

Example 2—Cream Shampoos

| Raw Ingredients | % | % | % | % | % | % |
|---|---|---|---|---|---|---|
| Fatty alcohol sulfates: Sodium lauryl, myristyl, cetyl, stearyl sulfate | 35.0 | 35.0 | 35.0 | 35.0 | 35.0 | 35.0 |
| Laureth-10 Stearate Acid | 9.0 | 9.0 | 9.0 | 9.0 | 9.0 | 9.0 |
| Carnauba Wax | 0.5 | | | | | |
| Jasmine Wax | | 0.5 | | | | |
| Mimosa Wax | | | 0.5 | | | |
| Bitter Orange Flower Wax | | | | 0.5 | | |
| Narcissus Wax | | | | | 0.5 | |

-continued

| Raw Ingredients | % | % | % | % | % | % |
|---|---|---|---|---|---|---|
| Wild Camomile Wax | | | | | | 0.5 |
| NaCl | 3.0 | 3.0 | 3.0 | 3.0 | 3.0 | 3.0 |
| Triethanolamine pure | 4.0 | 4.0 | 4.0 | 4.0 | 4.0 | 4.0 |
| 1,2-Dibromo-2,4-dicyano-butamine-2-phenoxy-ethanol | 0.1 | 0.1 | 0.1 | 0.1 | 0.1 | 0.1 |
| Water to make | 100.0 | 100.0 | 100.0 | 100.0 | 100.0 | 100.0 |

The formula in accordance with the invention leads to a visibly significant increase of the luster and an improvement of the combability of the hair.

Example 3—Intensive Hair Conditioning

| Raw Ingredients | % | % | % | % | % | % |
|---|---|---|---|---|---|---|
| Glycerinmonostearate, neutral | 6.0 | 6.0 | 6.0 | 6.0 | 6.0 | 6.0 |
| Lanolin alkoxylate | 2.0 | 2.0 | 2.0 | 2.0 | 2.0 | 2.0 |
| Carnauba Wax | 1.0 | | | | | |
| Jasmine Wax | | 1.0 | | | | |
| Mimosa Wax | | | 1.0 | | | |
| Bitter Orange Flower Wax | | | | 1.0 | | |
| Narcissus Wax | | | | | 1.0 | |
| Wild Camomile Wax | | | | | | 1.0 |
| Cetyl Alcohol | 2.0 | 2.0 | 2.0 | 2.0 | 2.0 | 2.0 |
| Mixture of Lanolin alcohol and paraffin oil | 1.0 | 1.0 | 1.0 | 1.0 | 1.0 | 1.0 |
| Tris-(oligo-oxyethyl)-alkyl-ammonium phosphate | 1.5 | 1.5 | 1.5 | 1.5 | 1.5 | 1.5 |
| Hydroxy ethyl cellulose | 20.0 | 20.0 | 20.0 | 20.0 | 20.0 | 20.0 |
| Citric Acid | 0.1 | 0.1 | 0.1 | 0.1 | 0.1 | 0.1 |
| Sorbic Acid | 0.2 | 0.2 | 0.2 | 0.2 | 0.2 | 0.2 |
| Water to make | 100.0 | 100.0 | 100.0 | 100.0 | 100.0 | 100.0 |

After use of the intensive hair conditioning preparation in accordance with the invention, it can be rinsed out of the hair without problems, resulting in a good wet and dry combability and providing the hair with a good texture and a cared for appearance.

Example 4—Foam Conditioner with Stabilizer

| Raw Ingredients | % | % | % | % | % | % |
|---|---|---|---|---|---|---|
| PVP/Vinyl-imidazolin-iummethochloride-Copolymer | 5.0 | 5.0 | 5.0 | 5.0 | 5.0 | 5.0 |
| PVP/PVA-Copolymer | 1.0 | 1.0 | 1.0 | 1.0 | 1.0 | 1.0 |
| Polyoxy-ethylene-12-cetylstearyl alcohol | 0.15 | 0.15 | 0.15 | 0.15 | 0.15 | 0.15 |
| Perfume Oil | 0.10 | 0.10 | 0.10 | 0.10 | 0.10 | 0.10 |
| Candelilla Wax | 0.05 | | | | | |
| Jasmine Wax | | 0.05 | | | | |
| Mimosa Wax | | | 0.05 | | | |
| Bitter Orange Flower Wax | | | | 0.05 | | |
| Narcissus Wax | | | | | 0.05 | |
| Wild Camomile Wax | | | | | | 0.05 |
| Water to make | 100.0 | 100.0 | 100.0 | 100.0 | 100.0 | 100.0 |
| Propane/Butane 40/60 | 10.00 | 10.00 | 10.00 | 10.00 | 10.00 | 10.00 |

The foam conditioner creates a silky foam and improves the combability and the texture of the hair washed with it.

List of Reference Symbols for FIG. 1:
Coverage of hair surface with flower waxes
A basic formula
B basic formula with 1% apple wax
C basic formula with 1% mimosa wax
D basic formula with 1% jasmine wax

What is claimed is:

1. A liquid hair treatment composition in the form of a hair shampoo, a hair styling preparation or a hair spray, said hair treatment composition comprising water;

from 0.01 to 12 percent by weight of at least one wax ingredient selected from the group consisting of jasmine wax, mimosa wax, narcissus wax, bitter orange wax and wild camomile wax; and at least one conventional cosmetic ingredient for liquid hair treatment agents selected from the group consisting of anionic surfactants, cationic surfactants and propellants, with the proviso that no strongly oxidizing substance is present.

2. A method of treating hair consisting essentially of the steps of:

a) providing a liquid hair treatment composition comprising water, from 0.01 to 12 percent by weight of at least one wax ingredient selected from the group consisting of jasmine wax, mimosa wax, narcissus wax, bitter orange wax and wild camomile wax and at least one conventional cosmetic ingredient for liquid hair treatment agents selected from the group consisting of anionic surfactants, cationic surfactants and propellants, with the proviso that no strongly oxidizing substance is present; and b) applying said liquid hair treatment composition to the hair.

3. A hair shampoo comprising

35% by weight of at least one fatty alcohol sulfate selected from the group consisting of sodium lauryl sulfate, sodium myristyl sulfate, sodium cetyl sulfate and sodium stearyl sulfate;

9.0% by weight of stearic acid;

0.5% by weight of at least one wax ingredient selected from the group consisting of jasmine wax, mimosa wax, narcissus wax, bitter orange wax and wild camomile wax;

0.1% by weight of 1,2-dibromo-2,4-dicyanobutamine-2-phenoxyethanol;

4.0% by weight of triethanolamine;

3.0% by weight of sodium chloride; and water.

4. A hair spay for a humid climate, said hair spray comprising 0.05% by weight of at least one wax ingredient selected from the group consisting of jasmine wax, mimosa wax, narcissus wax, bitter orange wax and wild camomile wax;

2.00% by weight of vinyl acetate/crotonic acid copolymer;

0.16% by weight of 2-amino-2-methyl-1-propanol;

0.10% by weight of perfume oil;

37.84% by weight of ethyl alcohol; and propyl alcohol/butane as propellant.

5. A hair conditioning composition for intensive hair conditioning, said hair conditioning composition consisting of:

1.0% by weight of at least one wax ingredient selected from the group consisting of jasmine wax, mimosa wax, narcissus wax, bitter orange wax and wild camomile wax;

20.0% by weight of hydroxyethyl cellulose;

6.0% by weight of neutralized glycerol monostearate;

2.0% by weight of lanolin alkoxylate;

2.0% by weight of cetyl alcohol;

1.5% by weight of tris-(oligooxyethyl)alkylammonium phosphate;

1.0% by weight, of a mixture of lanolin alcohol and paraffin oil;

0.2% by weight of sorbic acid;

0.1% by weight of citric acid; and water.

6. A foam conditioner with stabilizer, said foam conditioner comprising 5.0% by weight of polyvinyl pyrrolidone/imidazoliniummethochloride copolymer;

1.0% by weight of polyvinyl pyrrolidone/polyvinyl acetate copolymer;

0.05% by weight of at least one wax ingredient selected from the group consisting of jasmine wax, mimosa wax, narcissus wax, bitter orange wax and wild camomile wax;

0.15% by weight of polyoxyethylene-12-cetyl stearyl alcohol;

0.10% by weight of perfume oil;

10.00% by weight of propane/butane, 40/60, as propellant; and water.

7. A hair treatment composition consisting of 2.0% by weight of cetyl alcohol;

1.0% by weight of mimosa or jasmine wax;

1.0% by weight of sorbitol stearate;

1.0% by weight of lanolin oil, isopropyl palmitate and/or castor oil;

1.0% by weight of paraffin oil;

2.0% by weight of glycerol;

1.0% by weight of lauryl alcohol polyethylene glycolic ether (20 EO);

2.0% by weight of cetyltrimethylammonium chloride solution, 25%; and water.

* * * * *